(12) United States Patent
Halder

(10) Patent No.: US 9,936,989 B2
(45) Date of Patent: Apr. 10, 2018

(54) DEVICE FOR BONE SUPPORT WITH IMPROVED ROTATIONAL STABILITY

(71) Applicant: GENERAL SURGICAL COMPANY (INDIA) PVT LIMITED, Tamil Nadu (IN)

(72) Inventor: Subhash Chandra Halder, Halifax (GB)

(73) Assignee: GENERAL SURGICAL COMPANY (INDIA) PVT LIMITED, Nadu (IN)

( * ) Notice: Subject to any disclaimer, the term of this patent is extended or adjusted under 35 U.S.C. 154(b) by 24 days.

(21) Appl. No.: 15/030,532

(22) PCT Filed: Oct. 21, 2014

(86) PCT No.: PCT/IN2014/000674
§ 371 (c)(1),
(2) Date: Apr. 19, 2016

(87) PCT Pub. No.: WO2015/059717
PCT Pub. Date: Apr. 30, 2015

(65) Prior Publication Data
US 2016/0256202 A1    Sep. 8, 2016

(30) Foreign Application Priority Data

Oct. 22, 2013 (IN) ............................ 4762/CHE/2013

(51) Int. Cl.
*A61B 17/72* (2006.01)
*A61B 17/74* (2006.01)

(52) U.S. Cl.
CPC ........ *A61B 17/7266* (2013.01); *A61B 17/725* (2013.01); *A61B 17/7283* (2013.01); *A61B 17/744* (2013.01)

(58) Field of Classification Search
CPC .............. A61B 17/7266; A61B 17/725; A61B 17/7283; A61B 17/744

(Continued)

(56) References Cited

U.S. PATENT DOCUMENTS 3,216,414 A * 11/1965 Street .................. A61B 17/746 411/446
3,791,380 A * 2/1974 Dawidowski ........ A61B 17/746 606/68

(Continued)

OTHER PUBLICATIONS

International Search Report of PCT/IN2014/000614, dated Feb. 6, 2015.

*Primary Examiner* — Pedro Philogene
*Assistant Examiner* — David C Comstock
(74) *Attorney, Agent, or Firm* — Leason Ellis LLP

(57) ABSTRACT

A bone support fixating device with a longitudinally slotted hip screw which permits operative compression of the fracture and holds this compression yet allows sliding as further compression of the fracture occurs under forces of weight bearing; comprising a hollow cylindrical shaft with a screw portion at its upper proximal end and four equally spaced longitudinal grooves at its lower distal end, having three equally distant angled holes between the ends, through which three wires can be inserted, the three 'elastic' proximally curved wires, welded, glued or crimped distally, can be inserted into the hip screw collectively called the 'tri-wire'; The proximal end has the wires curved outward, with all three wires equally spaced; upon pushing the tri-wire into the hip screw, the wires goes through the angle holes in the hip screw and provides three projections equally spaced; which improves the rotational stability of the proximal fracture fragment.

16 Claims, 12 Drawing Sheets

(58) Field of Classification Search
USPC .................................................... 606/62–68
See application file for complete search history.

(56) References Cited

U.S. PATENT DOCUMENTS

| | | | | |
|---|---|---|---|---|
| 4,805,607 | A | * | 2/1989 | Engelhardt ............ A61B 17/72 606/64 |
| 4,976,258 | A | * | 12/1990 | Richter .............. A61B 17/7283 606/64 |
| 8,353,910 | B2 | * | 1/2013 | Dell'Oca ............. A61B 17/744 606/64 |
| 8,409,205 | B2 | | 4/2013 | Yang et al. |
| 8,491,584 | B1 | * | 7/2013 | Fagan ................ A61B 17/7266 606/64 |
| 2006/0149247 | A1 | | 7/2006 | Frigg et al. |
| 2010/0094293 | A1 | * | 4/2010 | McClellan ......... A61B 17/7241 606/64 |
| 2011/0184472 | A1 | | 7/2011 | Niederberger |

* cited by examiner

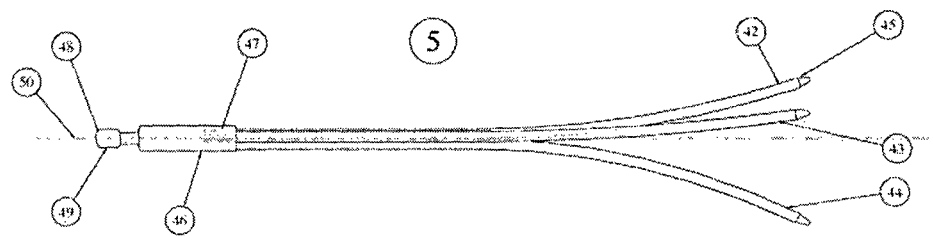
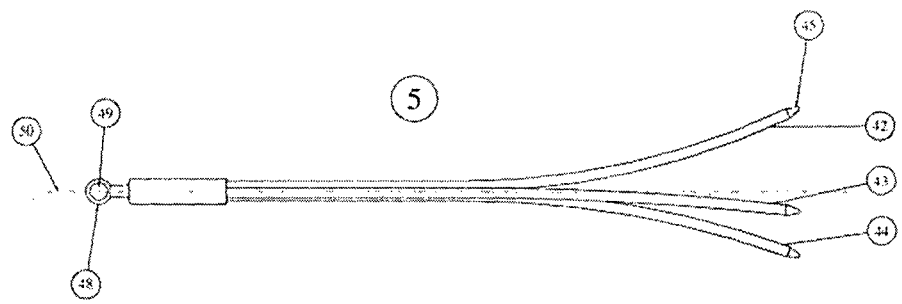
Figure 7
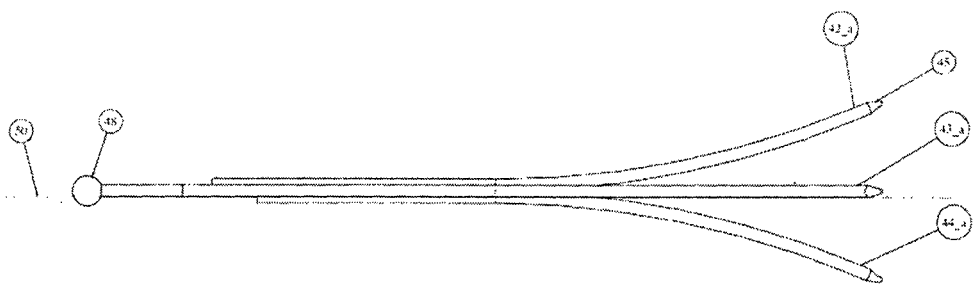
Figure 8

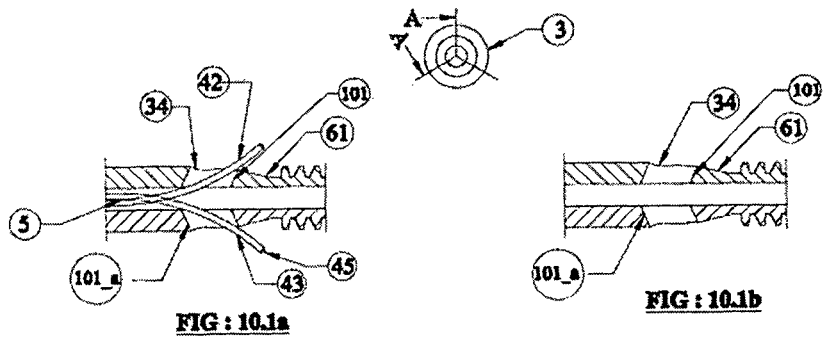
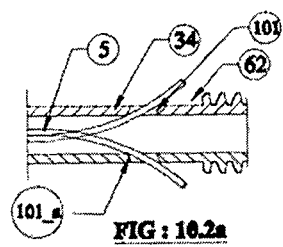
FIG: 10.1a
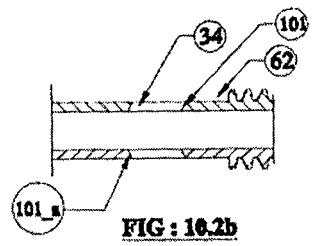
FIG: 10.1b
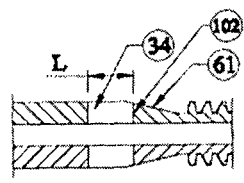
FIG: 10.2a
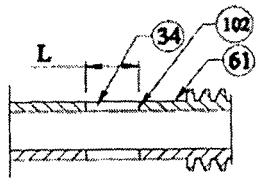
FIG: 10.2b
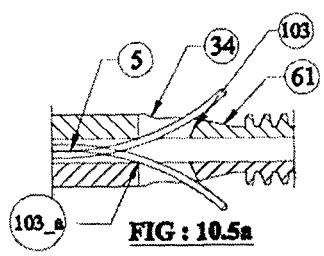
FIG: 10.3
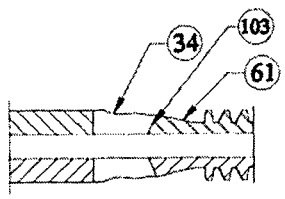
FIG: 10.3
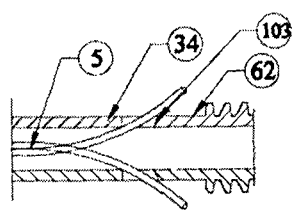
FIG: 10.5a
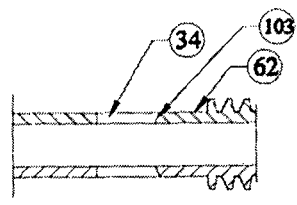
FIG: 10.5b
FIG: 10.6a
FIG: 10.6b

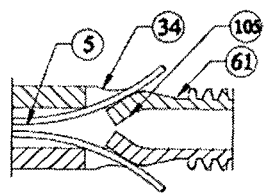
FIG: 10.7a
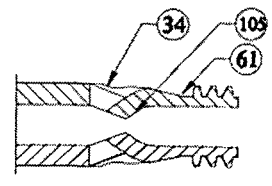
FIG: 10.7b
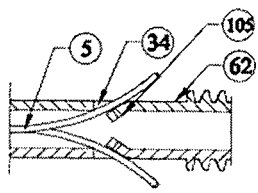
FIG: 10.8a
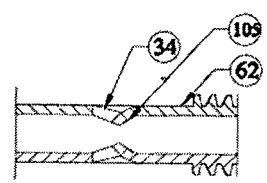
FIG: 10.8b
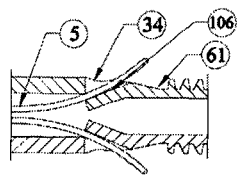
FIG: 10.9a
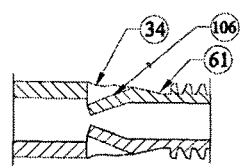
FIG: 10.9b
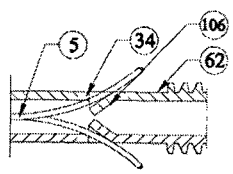
FIG: 10.10a
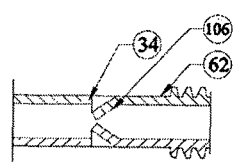
FIG: 10.10b
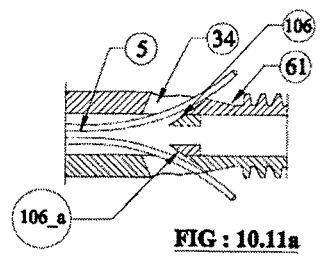
FIG: 10.11a
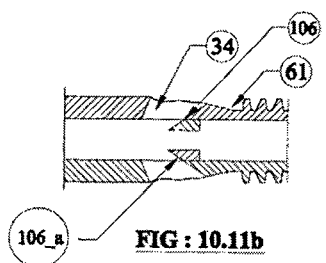
FIG: 10.11b
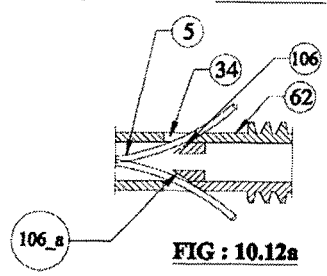
FIG: 10.12a
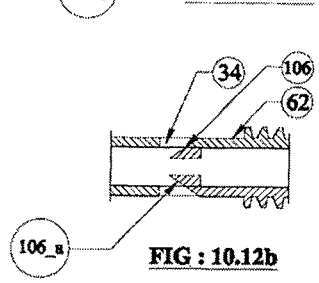
FIG: 10.12b

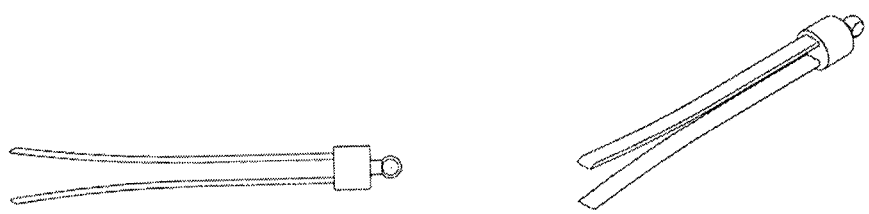
FIG 13.1
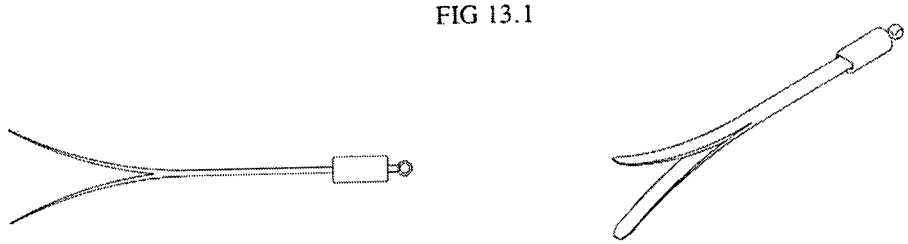
FIG 13.2
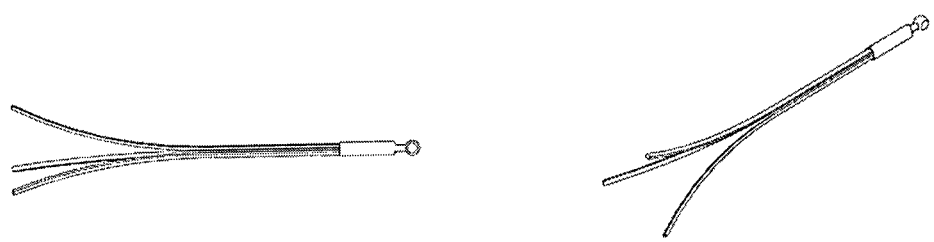
FIG 13.3
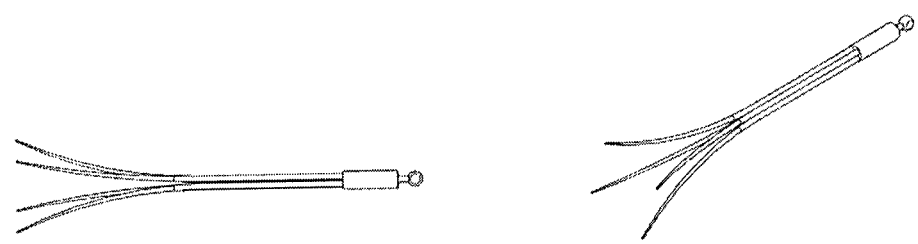
FIG 13.4

DEVICE FOR BONE SUPPORT WITH IMPROVED ROTATIONAL STABILITY

CROSS-REFERENCE TO RELATED PATENT APPLICATIONS

This application is a U.S. National Phase Application under 35 U.S.C. § 371 of International Patent Application No. PCT/IN2014/000674, filed Oct. 21, 2014, and claims the priority of Indian Application No. 4762/CHE/2013, filed Oct. 22, 2013, all of which are incorporated by reference in their entireties. The International Application was published on Apr. 30, 2015 as International Publication No. WO 2015/059717 A1.

FIELD OF THE INVENTION

The present invention particularly relates to an implant comprising of individual elements for the fixation of fractures of the femoral neck, trochanteric and subtrochanteric regions of the femur with improved rotational stability.

BACKGROUND OF THE INVENTION

Devices for fixing a femur facture in the vicinity of the hip joint are already known.

There are various devices in the market that can be used to fix fractures near the hip. These devices over the years have had several iterations so as to try to improve the rotational stability of the hip fracture. Some of the nail designs include incorporating two hip screws instead of one, reamer like threads on the screw and augmentation of cement. Augmenting cement has the disadvantage that it's almost impossible to remove the hip screw if required without damaging the hip. The current designs in the market suffer from disadvantages, the major being that they have not been proved to improve rotational stability of the fracture. Also, the fact that the design iterations are frequent raises questions about rotational stability of the fracture fragment.

Intermedullary nailing systems in the present suffer from the disadvantage that they cannot be used for intracapsular fractures by the closed intermedullary method.

The present invention seeks to overcome the disadvantages regarding rotational stability and treatment for intracapsular fractures by the closed intermedullary method.

PRIOR ART

The information relating to bone support by the inventor of the present invention is disclosed in the following patents:

GB 2209947 A titled "DEVICE FOR FIXING FEMUR FRACTURES" provides for a device for use in the treatment of fractures of the femoral neck, trochanteric and subtrochanteric regions of the femur incorporates a smoothly curved intramedullary rod which can be introduced into the femoral shaft through the great trochanter, a hip screw which can be introduced into the femoral neck (through the outer cortex of the femur) through a fixing hole in the intramedullary rod and into the cancellous bone of the femoral neck and head; and a set screw housed in the intramedullary rod to engage the hip screw. The set screw may engage in one of a plurality of longitudinal grooves in the hip screw to allow limited axial movement of the hip screw through the hole in the intramedullary rod. The rod may be provided with a cloverleaf section to help prevent rotation relative to the femoral shaft. The device is suitable for both left- and right-handed femurs.

US 20070288016 A1 titled "BONE SUPPORT" provides for A bone support is provided comprising: a hollow elongate rod having trailing and leading ends; said hollow rod being insertable along at least a substantial part of the length of the interior of a bone; an elongate fixing device positioned within said hollow rod, the elongate fixing device having trailing and leading ends, the leading end of said elongate fixing device having a plurality of projections which can be extended out of the rod to engage with bone surrounding the leading end of the rod, thus acting as a bone rotation prevention means; said elongate fixing device being operable from the trailing end of the rod; the leading end of the rod having side apertures; and the bone support including an end plug having inner and outer ends; the inner end of the plug having inwardly tapered surfaces adjacent to said side apertures which surfaces engage with the projections of the elongate fixing device when the fixing device is moved within the rod, towards the leading end of the rod, engagement of the projections with the tapered surfaces guiding the projections out of said side apertures, and causing the projections to splay outwardly and penetrate bone surrounding the leading end of the rod.

GB2256802 A titled "IMPROVEMENTS IN OR RELATING TO BONE SUPPORT" The support comprises a hollow, elongate open-ended nail which is inserted particularly in a humerus bone, fixing wires being inserted through the nail and embedded in the head of the bone. At a distal end of the nail a distal fixing screw passes through the posterior cortex of the bone to the anterior cortex via the nail to inhibit rotational movement of the distal end of the bone relative to the nail. The outward movement of the fixing wires has a piercing effect which causes minimal disturbance to the proximal end of the bone, but also effectively locks the proximal end to the nail, preventing relative rotation of that end.

Therefore there is a need for a device that improves the rotational stability of an existing intermedullary implant that can be used for proximal end of the femur including intracapsular fracture which is easy to implant and that can be easily removed without damaging the surrounding bone.

SUMMARY OF THE INVENTION

The object of the present invention is to provide an implant comprising of individual elements for bone support in the form of an elongated hollow rod commonly referred to as intermedullary 'nail' with increased rotational stability of the fracture fragment around the hip area than devices in the prior art.

It is a further object of the present invention to provide an intermedullary device that can also fix intracapsular fracture. Yet another feature of this invention is to provide a bone support which is easy to manufacture. Yet another objective is to implant the device easily and percutaneous. It is also a further object of the present invention to provide a hip screw that can be easily removed without damaging the surrounding bone. It is also a further object of the present invention to be able to insert the device using the same targeting device used by the hip screw.

BRIEF DESCRIPTION OF THE INVENTION

The present invention comprises of an implant having individual components (i) an elongate device that consist of a three 'elastic' proximally curved wires, that can be inserted into the hip screw, (ii) a hip screw which consists of an end cap at the distal end and (iii) a set screw incorporated at the proximal end.

This invention relates to an implant comprising of individual elements resulting in a smoothly curved rod closely fitting the internal geometry of the upper femoral shaft which can be inserted into the medullary canal of the intact femur making it suitable for fixing all fractures which may be encountered in the neck, trochanteric or subtrochanteric regions of the femur hereinafter referred to as the elongated element. This element can also fix intracapsular fractures.

The elongated element of the present invention can be inserted through two small incisions which do not cut muscle significantly or disturb the fracture haematoma. The implant of the present invention comprises of has a longitudinally slotted hip screw which permits operative compression of the fracture and holds this compression yet allows sliding as further compression of the fracture occurs under forces of weight bearing. This comprises of a hollow cylindrical shaft or elongated device with a screw portion at its upper proximal end and four equally spaced longitudinal grooves at its lower distal end. Between these ends are three equally distant angled holes through which three wires can be inserted.

The elongate element consists of three 'elastic' proximally curved wires, welded, glued or crimped distally, that can be inserted into the hip screw. This is collectively called the 'tri-wire'. The proximal end of the tri-wire has the wires curved outward, with all three wires equally spaced. Upon pushing the tri-wire into the hip screw, the wires goes through the angle holes in the hip screw and provides three projections equally spaced. This improves the rotational stability of the proximal fracture fragment. This will not prevent any dynamisation of the fracture. This added tri-wire will improve healing fracture due to better rotational stability. The elongate element consists of a ball at the distal end of the tri-wire and can be removed easily.

The hip screw consists of an end cap at the distal end over the ball of the tri-wire to prevent distal migration of the tri-wire.

The set screw incorporated in the proximal end of the nail sits in the longitudinal slots of the hip screw to prevent rotation of the hip screw.

DETAILED DESCRIPTION OF THE INVENTION

An implant or a fixating device with a smoothly curved rod closely fitting the internal geometry of the upper femoral shaft which can be inserted into the medullary canal of the intact femur making it suitable for fixing all fractures which may be encountered in the neck, trochanteric or subtrochanteric regions of the femur. This device can also fix intracapsular fractures. The said implant can be inserted through two small incisions which do not cut muscle significantly or disturb the fracture haemotoma.

The said device with a longitudinally slotted hip screw which permits operative compression of the fracture and holds this compression yet allows sliding as further compression of the fracture occurs under forces of weight bearing. This device comprises of a hollow cylindrical shaft with a screw portion at its upper proximal end and four equally spaced longitudinal grooves at its lower distal end. Between these ends are three equally distant angled holes through which three wires can be inserted. This elongate device which consists of three 'elastic' proximally curved wires, welded, glued or crimped distally, that can be inserted into the hip screw. This is collectively called the 'tri-wire'. The proximal end of the tri-wire has the wires curved outward, with all three wires equally spaced. Upon pushing the tri-wire into the hip screw, the wires goes through the angle holes in the hip screw and provides three projections equally spaced. This improves the rotational stability of the proximal fracture fragment. This will not prevent any dynamisation of the fracture. This added tri-wire will improve healing fracture due to better rotational stability. The elongate device consists of a ball at the distal end of the tri-wire, which is easily removeable.

The hip screw consists of an end cap at the distal end over the ball of the tri-wire to prevent distal migration of the tri-wire.

The set screw incorporated in the proximal end of the nail sits in the longitudinal slots of the hip screw to prevent rotation of the hip screw.

DESCRIPTION OF FIGURES

FIG. 7: Elongate device with its various components.

FIG. 8: Tri-wire where in one of the wires is longer than the other.

FIG. 10: Various embodiments of tapered neck, straight neck, elongated tear drops and slots.

FIG. 13: Various options to the tri-wire.

DETAILED DESCRIPTION OF THE DRAWINGS

Figure 1:
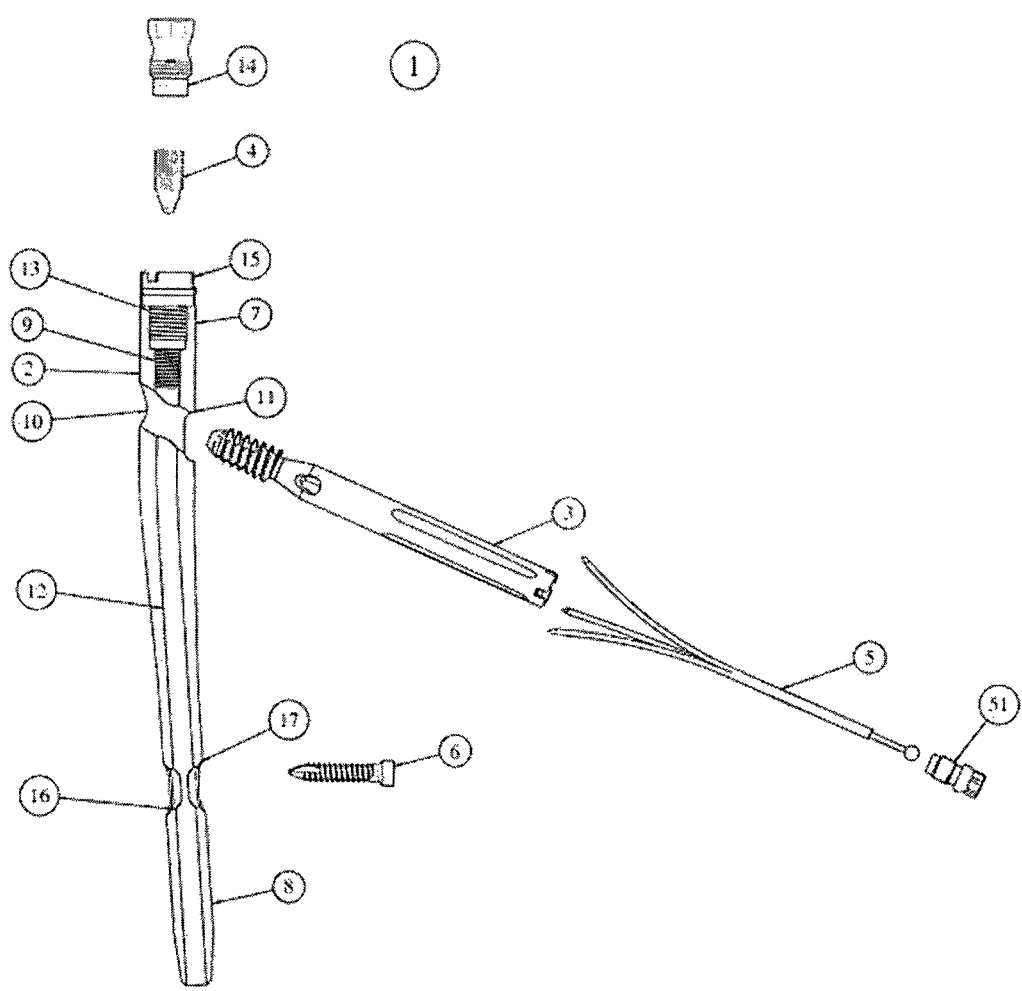
FIG. 1: The fixating device illustrated in an unassembled state.

In FIG. 1, a fixating device 1 is illustrated in an unassembled state. This comprises generally of the intramedullary rod 2, an extended hip screw 3, a set screw 4, an elongate device collectively called the 'tri-wire' 5 and either a locking screw 6.

The intramedullary rod 2 comprises of an upper cylindrical proximal portion 7 and lower distal portion 10. The upper end of the proximal portion 7 has a threaded hole 9 through which a threaded set screw 4 passes in order to secure the hip screw 3. Towards the bottom of the proximal portion 7, the length of which is approximately ⅓ of the total length of the rod 2, is an upwardly inclined hip screw receiving hole 10 such that the hip screw 3 can be fixed through the hole 10 with a threaded part of the hip screw entering the hip bone. The edges of the inclined hole 10 that meet at the proximal portion 7 has a 'C' shaped surface 11. The intramedullary rod 2 is, in this embodiment, provided with a narrow bore 12 formed through the lower part of the proximal portion of the rod and through the complete distal portion of the rod. The function of such a narrow bore 12 is to minimise the use of materials and to provide a fixating device 1 which is as light as reasonably possible. In addition to the set screw receiving female thread 9 the intramedullary rod 2 also consists of an end cap receiving threaded portion 13, through which an end cap 14 travels through. The end cap receiving threaded portion 13 is larger in diameter than the set screw receiving female thread 9. The rod 2 consists of three openings i.e. slots 15 at the proximal end to allow for it to be held by an instrument. The hip screw 3 is located within the inclined fixing hole 10 and the set screw 4 located within the threaded bore 8 so that the smoothly rounded lower end 37 of the set screw can be located within one of the four grooves 27 of the proximal end of the hip screw 3. In this manner the fixating device 1 can be fitted to a patient with the hip screw located in the ideal position with respect to the fixing hole 10, though if the fracture shortens the set screw will not prevent desirable sliding of the hip screw 3 in the fixing hole 10 of the rod 2. The elongate device which will now be collectively called as a tri-wire 5 shown in FIG. 1 has three projections 42, 43, 44 with chamfered or rounded tips 45 (described in greater detail in FIG. 7). The objective when using the bone support is to arrange the projections 42, 43, 44 to be moved through the three tear drop slots 34 in the hip screw 3, so that these projections penetrate bone surrounding the leading end of the bone support to prevent rotation. The invention is also concerned with the way in which the projections 42, 43, 44 are guided out of the tear drop holes 34 on the hip screw 3.

Figure 2:
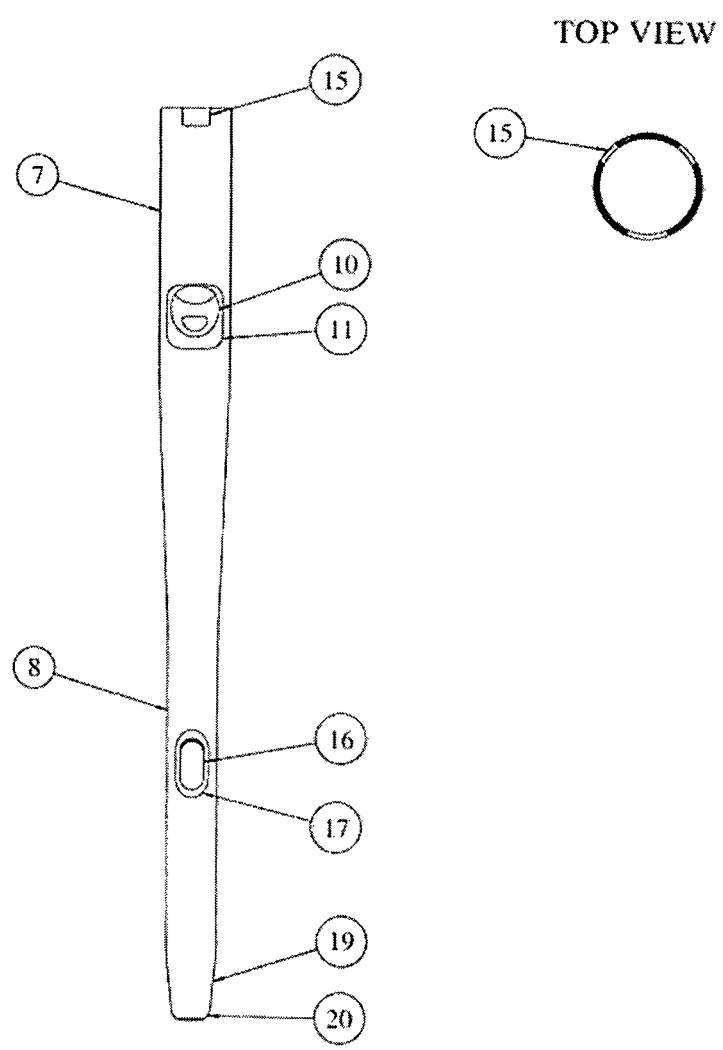
FIG. 2: Top view of the intramedullary rod.

FIG. 2 clearly shows the three openings i.e. slots 15 in the rod at the proximal end in the top view shown. The distal end of the intramedullary rod 2 comprises of a conical section 19 with a smoothly rounded end 20. In this, preferred, embodiment, towards the distal end of the rod 2 is located a horizontal oblong slot 16 formed through the distal cross, section. The edges of the oblong slot 16 are formed with smoothly curved surfaces 17.

Figure 3:
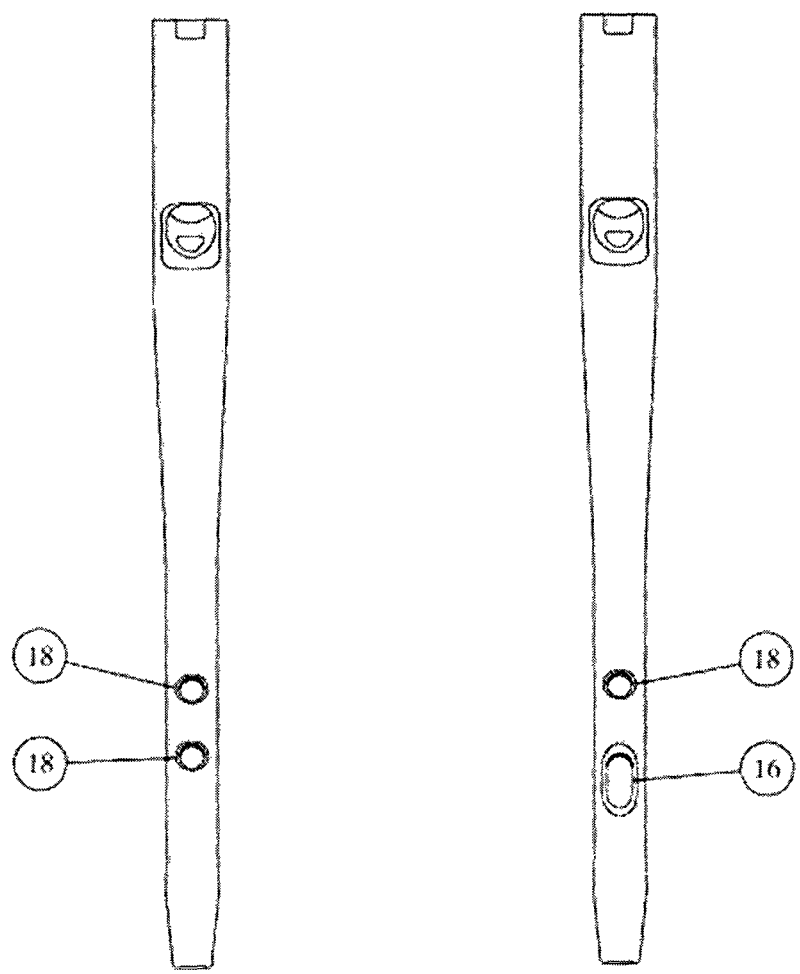
FIG. 3: Placement of the different shaped openings on the intramedullary rod.

In other forms of the intramedullary rod 2, there could be a pair of holes 18 or a single hole 18 and an oblong slot 16, both of which are shown in FIG. 3.

Figure 4:
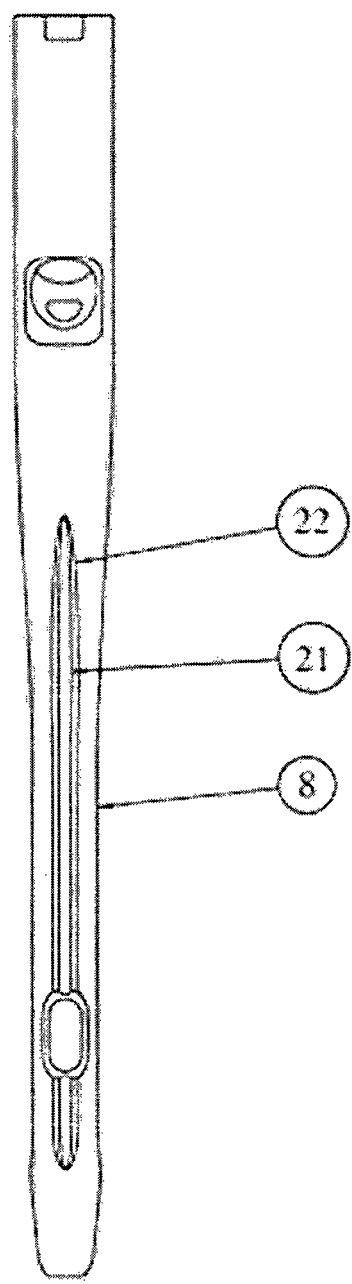
FIG. 4: Placement of the grooves in the intramedullary rod.

In the embodiment shown in FIG. 4, three equally spaced elongated V-grooves 21 formed along the exterior face of the distal portion 8 of the rod, so as to provide a cloverleaf like cross section. As with the inclining fixing hole 10, the edges around the respective V-grooves 21 are formed with smoothly curved surfaces 22. The current embodiment consist of a smooth distal surface 8 as shown in all figures expect for FIG. 4.

Figure 5:
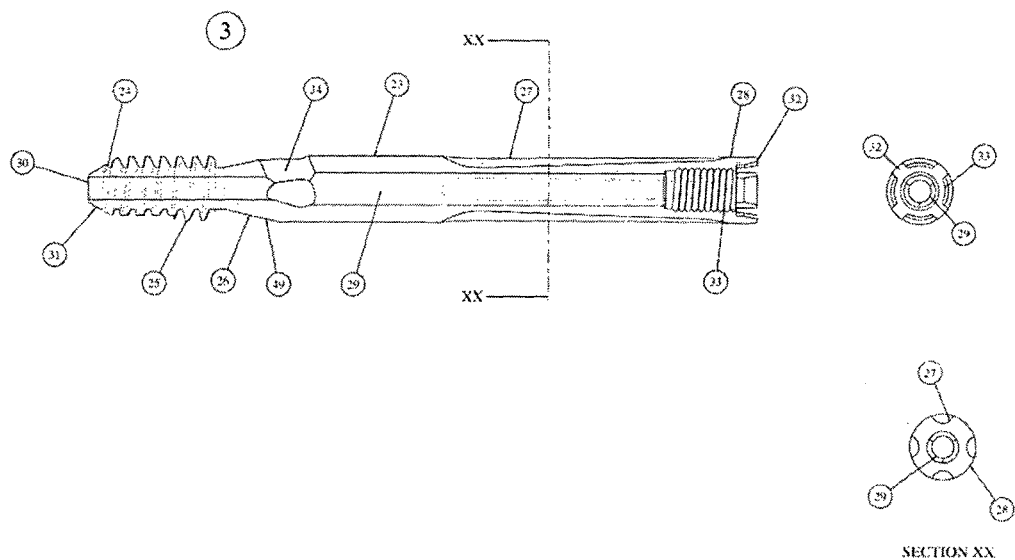
FIG. 5: The hip screw with its various components.

FIG. 5 shows a hip screw 3 that comprises of a hollow shaft 23 having a self-tapping 24 threaded portion 25 at its proximal end 26 and four equally spaced longitudinal grooves 27 at its distal (lower) end 210. The grooves 27 have variable heights at different points to aid in dynamisation. This is clearly shown in FIG. 5. The hip screw 3 is provided with a narrow longitudinal bore 29 from one end of the screw to the other so as to save on materials and weight. The current embodiment shown in FIG. 5 consists of two co-axial bores 29. In the current embodiment the hip screw 3 is provided with a substantially flat distal end face 30 with a mild chamfering or rounding 31 as shown in FIG. 5 so that any possibility of post-operative perforation of the cortex of the femoral head is minimised. In addition the distal end of the hip screw includes four cruciate slots 32 and wide threaded bore 33. The arrangement of the cruciate slots 32 and wide threaded bore 33 of the hip screw will be more clearly understood with reference to the right side of FIG. 5 of the drawings.

Figure 6:
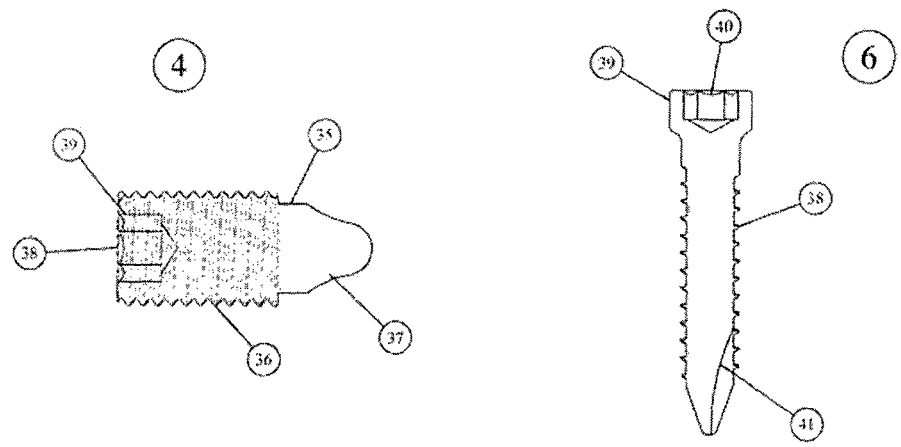
FIG. 6: The screw set with its various components.

In FIG. 6, the set screw 4 comprises a solid shaft 35 which has a threaded upper end 36 and smoothly rounded ball-nose lower end 37, there being a hexagonal hole 38 formed through the top face of the shaft 39 to receive an Allen key.

Referring now to FIG. 6, locking screw 6 comprises of a threaded shaft portion 38, an enlarged head portion 39 with a hexagonal hole 40 formed through the top face to receive an Allen key and a self-tapping threaded end 41.

The elongate device is constructed by welding together three stainless steel wires 42, 43, 44 as seen clearly in FIG. 7. The wires are pre-sprung, flared and strong. The current embodiment consists of a rod 46 which consists of three holes 47 into which the stainless steel wires are inserted and welded, brazed, soldered, crimped or press-fit. This rod consists of an enlarged head 48, in this case a ball-ended tip with a flat milled 49, which facilitates in manipulation. The current embodiment is considered superior for manipulation as the axis of the ball 48 is directly on the longitudinal axis of the rod, thereby at the centre of the axis of the elongate device 50.

Other embodiments of this tri-wire 5 could consist of three wires 42_a, 43_a and 44_a with the longest wire (44_a) terminating in an enlarged head 48 as shown in FIG. 8. This particular embodiment suffers from the disadvantage that the enlarged head 48 is not along the longitudinal axis 50 of the elongate device 3. This makes the manipulation of this embodiment more difficult than the preferred embodiment.

Figure 9:
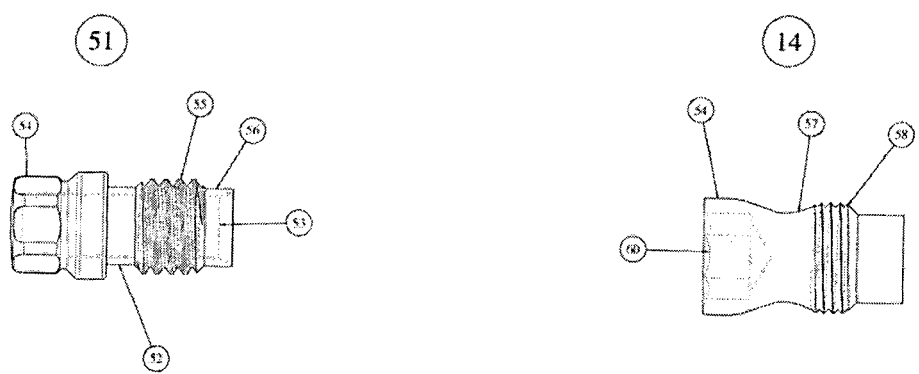
FIG. 9: End cap with its various components.

As shown in FIG. 1 the hip screw 3 consists of an end cap 51 at the distal end over the ball of the tri-wire to prevent distal migration of the tri-wire. The end cap as shown in FIG. 9 consists of a shaft 52 with a hole 53 to take the ball 49 of the elongate device 5 such that the elongate device is extractable. It also consists of a hexagonal head 54 and a threaded portion 55 with a step down at the end 56 for ease of entry into the distal thread bore 33 in the hip screw 3.

As shown in FIG. 9 the nail end cap 14 consists of a solid shaft (57), threaded portion (58), an enlarged head (59) flat top surface and an Allen key receiving hexagonal hole (60). The end cap 14 is secured to the intramedullary rod 2 through the threaded hole 13.

The FIGS. 10.1 to 10.12 show scrap transverse sectional views of the hip screw 3 showing in particular the various types of holes/slots for the tri-wire projections 42, 43, 44.

FIG. 10.1a show a scrap views of the hip screw 3 with the current and most preferred embodiment where the holes are in the form of an elongated tear drop (34) at a forward angle on the tapered neck 61 of the hip screw 3 with a wedge shaped leading edge 101 with the tri-wire 5 installed. The chamfered / rounded tips 45 of the wires 42, 43 and 44 move along the rod in the direction of the hip screw 3 and engages with the wedge shaped leading edge 101 and thus brings about the necessary guiding. The back edge 101_a is also angled so that there is minimal stress concentration at the pivot point of the wires with respect to the back edge 101_a. The length of each slot can be shortened there by providing greater constraint to each wire as it emerges from the rod to engage the bone. FIG. 10.1b shows the above scrap view of the hip screw 3 without the tri-wire 5.

An alternative embodiment shown in FIG. 10.2a and FIG. 10.2b could have a straight neck 62 on which the three tear-drop shaped holes (34) are placed, with a leading edge 101.

FIG. 10.3 shows an elongate slot in the walls of the hip screw rod 2 having a length 'L' facing radially. With simple square ends 102, as shown in FIG. 10.3, the slot length L must be relatively long to provide a guiding means which allows the end of the associated projection to be pushed through the slot and out into surrounding bone. This is less than ideal as the slot then pivots the length of the slot as forces parallel to the longitudinal axis of the rod and bone are applied to the bone. The fit between the projection and slot should preferable be snug as possible with minimum clearance. FIG. 10.3 shows the current and preferred embodiment of the hip screw 3 with a taper 61, whereas FIG. 10.4 shows the hip screw with a straight neck 62.

FIG. 10.5 a shows a second preferred embodiment where the tri-wire 5 has a forward angle leading edge 103 and a straight square back edge 103_a. This is similar to the embodiment shown in FIGS. 10.1a, 10.1b, 10.2a and 10.2b. This embodiment suffers from the disadvantage that the stress concentration at the pivot point of the tri-wire 5 with respect to the back edge 103a is higher than that of the stress concentration caused by the back edge 101_a in FIG. 10.1a. FIG. 10.5b shows the second preferred embodiment without a tri-wire 5 for clarity. FIGS. 10.6a and 10.6b show a hip screw 3 with a straight neck 62.

FIGS. 10.7a, 10.7b, 10.8a and 10.8b show a third preferred embodiment of the hip screw 3 with a tapered neck 61 and a straight neck 62. The slots are formed by machining and are shorter than the previous embodiments. The leading edge of each slot 105 is swaged inward radially, thereby provides more effecting guiding means. These is greater assurance that the leading edge of each wire will find the guiding means through the slot and the slot dimensions can be closer to the wire diameter.

FIGS. 10.9a, 10.9b, 10.10a and 10.10b show a fourth preferred embodiment of the hip screw 3 with a tapered neck 61 and a straight neck 62. The wall of the hip screw 3 is cut but with no significant material is removed by this incision to the wall of the rod. The leading side of the incision is the swaged inwards 106 leading a longitudinally facing window in through which the wire emerges. The guiding means is provided by the shaped leading end of the wire and the inwardly deformed edge of the exit window.

FIGS. 10.11a, 10.11b, 10.12a and 10.12b show a fifth preferred embodiment with the hip screw 3 with a tapered neck 61 and a straight neck 62. The hip screw 3 is provided with an annular member 107 fitted within the hip screw 3. The annular member 107 has shaped surface 107_a arranged to cooperate with the wires.

Since the annular member 107 projects inwardly of the hip screw 3, the leading edges of the wires engage the annular member before they reach the opening in the wall of the hip screw 3. I.e. a tunnel is created which gives further support to the emerging wire, minimising movement relative to the hip screw in all directions. This effect could be achieved in several ways. A precise plug could be fitted into the end of the hip screw 3, although in the embodiment shown, the annular member comprises a sleeve welded inside the rod. In yet another alternative separate inserts which fit the machine slots could be separately welded, brazed, soldered or snug fit into place.

Although the embodiments shown in FIGS. 10.11a, 10.11b, 10.12a and 10.12b involve more expensive manufacturing, this embodiment could provide maximum control over movement between wire and the hip-screw and this could be important in affecting bone healing.

Where a wire emerges from a slot with much clearance between the outside diameter of the wire and the inner slot dimensions, there is scope for movement. Where a wire emerges through a close fitting slot or hole there is substantially less opportunity for movement. Where a wire emerges from a close fitting tunnel such as that created with the embodiment shown in FIGS. 10.11a, 10.11b, 10.12a and 10.12b, least movement can be expected.

Figure 11:
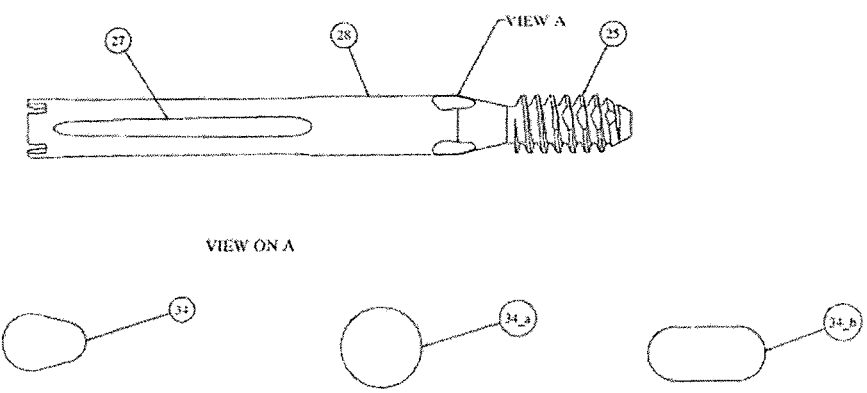
FIG. 11: Variables to openings on the intramedullary rod

A view of the current embodiment and the preferred embodiment, the tear-drop shaped hole 34 is shown in FIG. 11 along with other embodiments such as a less preferred straight hole 34a and a slot 34b.

Figure 12:
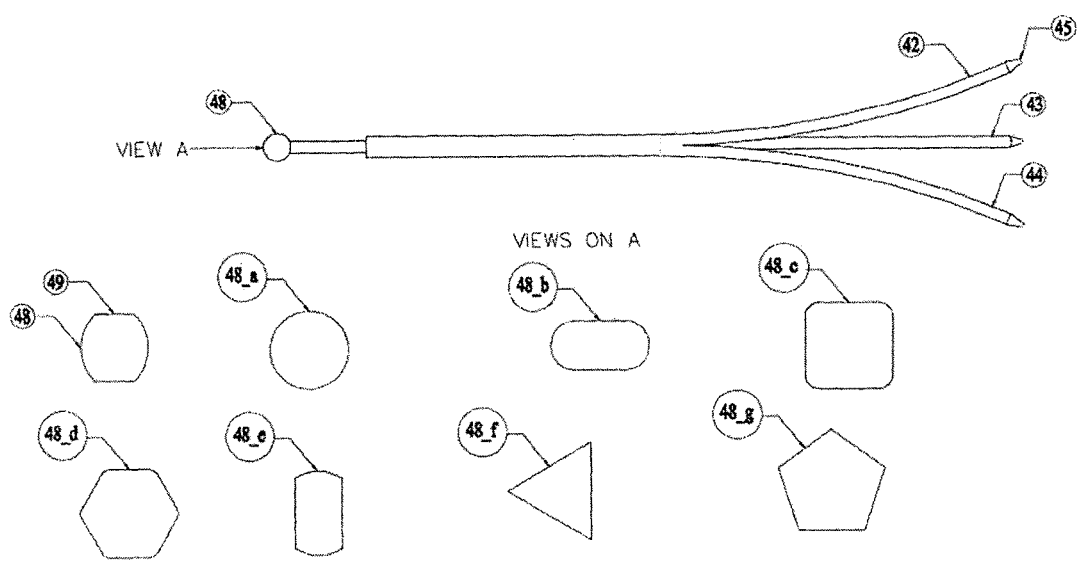
FIG. 12: Various types of enlarged head.

FIG. 12 shows a back view of the tri-wire 5 showing in particular different types of enlarged heads (48). Some of these shapes offer superior manipulation properties as some have a larger flat surface area coverage. However some of these are expensive to manufacture and use a larger diameter rod (46).

FIG. 13 shows different possible forms of the elongate device. FIGS. 13.1 and 13.2 shows two flat pre-sprung flats which would project through the hip screw 3. FIG. 13.1 shows two distinct and separate flat pre-sprung flats which are not welded to each other but welded only at the hip screw, which consist of two holes or slots. FIG. 13.2 shows two flat pre-sprung flats which are welded to each other for a minimum length and then separates. In this case the hip screw consists of one hole or slot. FIG. 13.3 consist of three square cross-section wires instead of round wires, with three slots or holes. FIG. 13.4 consist of four wires instead of three wires and the hip screw would also consist of four holes or slots 34.

Figure 14:
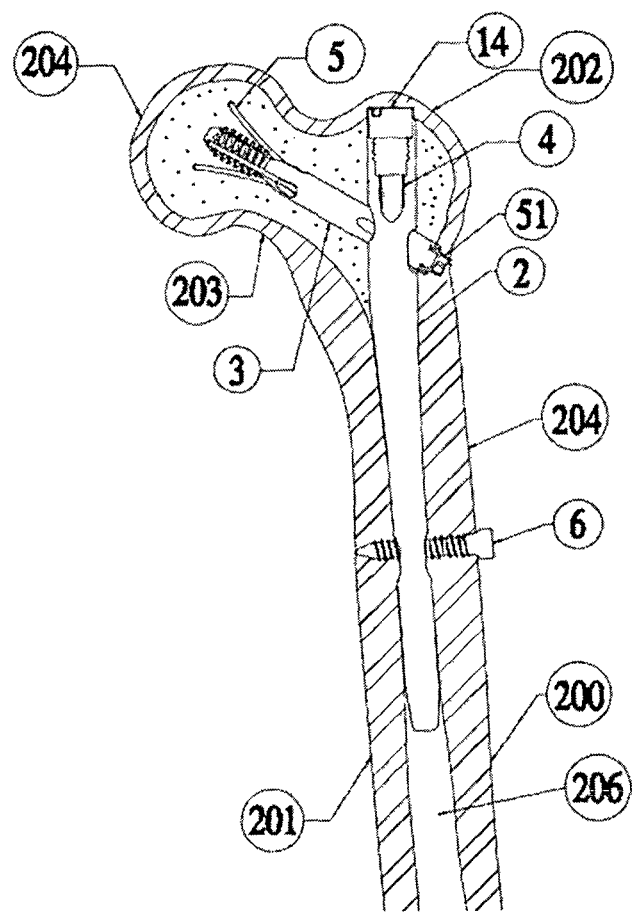
FIG. 14: Placement of the fixating device in the femoral head, trochanter and femoral neck.

In FIG. 14), a femur (200) comprises a femoral shaft (201), at the top of which is located the great Trochanter (202) which leads into the femoral neck (203) and the substantially spherical femoral head (204). The femoral shaft (201) consists of a hard outer cortex (205) and a medullary canal (206).

Preferred Embodiments:

The intramedullary rod 2, in this case, is approximately 200 mm long and the proximal 7 diameter is 15.5 mm. However in other embodiments it may be chosen from any diameter in the range of 12 mm to 17 mm. The diameter of the distal portion 8 in this case is 11 mm although in other embodiments it could be between 8 and 15 mm. The angle between the axis of the distal end of the rod and the axis of the inclined fixing holes 10 is approximately 125 degrees, but in other embodiment the angle may be chosen from anywhere in the range 115 to 150 degrees. The length of the horizontal slot is 10 mm although there could be a pair of holes spaced apart or an oblong hole and a hole as shown in FIG. 3.

In this, preferred, embodiment the axis of the upper proximal portion 7 over rod 2 is not coaxial with the axis of the lower distal portion 8 of the rod 2, but is at an angle of 4°. In other embodiments, this angle may be different.

In this embodiment the hip screw 3 consists of three equidistant angled tear-drop shaped holes 34 for the elongate device 5. Other embodiments could contain different slot configurations that could be used for the elongate device 5. The hip screw 3 has a diameter of 10.5 mm and a length selected from 60 mm to 140 mm in increments of 5 mm. Although different diameters could be chosen if required.

The diameter of the current locking screw is approximately 4.5 mm, and may change in other embodiments. However the length will need to be chosen such that the head will project outside the shaft of the femur and the self-tapping portion 41 will cut a path into the opposing wall of the femur.

Although embodiments of this invention have been shown and described, it is to be understood that various modification and substitutions, can be made by those skilled in the art without departing from the novel spirit and scope of the invention.

I claim:

1. A bone support fixating device, the device comprising:
    a hollow intramedullary rod;
    an extended hip screw;

a set screw;
an elongate device;
a locking screw;
the intramedullary rod comprising an upper cylindrical proximal portion and a lower distal portion; wherein the upper end of the proximal portion having a threaded hole through which a threaded set screw passes in order to secure the hip screw towards the bottom of the proximal portion;
an upwardly inclined hip screw receiving hole adapted to fix the hip screw through the hole with a threaded part of the hip screw entering the hip bone;
a narrow bore formed through a lower part of the proximal portion of the intramedullary rod and through the complete distal portion of the rod;
an end cap receiving threaded portion adapted to receive an end cap, wherein a diameter of the end cap receiving threaded portion is larger than a diameter of the set screw receiving female thread;
wherein the hip screw comprising a hollow shaft having a self-tapping threaded portion at a proximal end of the hollow shaft and four equally spaced longitudinal grooves at a distal end of the hollow shaft; wherein the four equally spaced longitudinal grooves are having variable heights at different points that aids in dynamization of the fracture;
wherein the distal end of the hip screw having four cruciate slots and wide threaded bore;
an end cap at the distal end over the ball of the elongate device to prevent distal migration of the elongate device, wherein the end cap comprising of a shaft with a hole to take the ball of the elongate device in a manner that the elongate device is extractable; wherein the end cap further comprising of a hexagonal head and a threaded portion with a step down at the end that enables the entry into the distal thread bore in the hip screw, the hip screw being located within the inclined fixing hole;
wherein the set screw being located within the threaded bore in a manner that the smoothly rounded lower end of the set screw is adapted to lock within one of the four grooves of the proximal end of the hip screw that ensures the fixating device is fitted to a patient with the hip screw located in the ideal position with respect to the fixing hole;
wherein the elongated device comprising of a rod that consisting of an enlarged head, a ball-ended tip with a flat milled for easy manipulation as the axis of the ball is directly on the longitudinal axis of the rod, thereby at the centre of the axis of the elongate device; being positioned to move through the three tear drop slots in the hip screw; in such a manner as to enable these projections to penetrate the bone surrounding the leading end of the bone support to prevent rotation;
a nail end cap comprising of a solid shaft, threaded portion, an enlarged head flat top surface and an Allen key receiving hexagonal hole, being secured to the intramedullary rod through the threaded hole; the projections being guided out of the elongated tear drop slots on the hip screw;
the elongated tear drop slots being placed on a tapered neck at a forward angle on the tapered neck of the hip screw with a wedge shaped leading edge; the tips of the wires moving along the intramedullary rod in the direction of the hip screw.

2. The device as claimed in claim 1, wherein the intramedullary rod comprises of three opening, wherein the three openings are located at the distal end of the intramedullary rod being circular, formed through the distal cross section, wherein the edges are formed with smoothly curved surfaces.

3. The device as claimed in claim 1, wherein the intramedullary rod comprises of three opening, wherein the three openings are located at the distal end of the intramedullary rod, being a combination of circular and oblong, formed through the distal cross section, wherein the edges are formed with smoothly curved surfaces.

4. The device as claimed in claim 1, wherein an axis of the upper cylindrical proximal portion over intramedullary rod is at an angle of 4°.

5. The device as claimed in claim 1, wherein tapered neck of the hip screw is substituted with a straight neck.

6. The device as claimed in claim 1, wherein an elongate slot is located in the walls of the intramedullary rod having a length 'L' facing radially with square ends; the elongate slot length L being of length sufficient to provide a guiding means, allowing the end of the associated projection to be pushed through the elongate slot and into the surrounding bone; the fit between the projection and elongate slot be snug as possible with minimum clearance.

7. The device as claimed in claim 1, wherein the elongate device is a tri-wire having a forward angle leading edge and a straight square back edge.

8. The device as claimed in claim 1, wherein the set screw comprises a solid shaft having a threaded upper end and smoothly rounded ball-nose lower end, wherein a hexagonal hole is formed through the top face of the shaft to receive an Allen key; the locking screw comprising a threaded shaft portion, an enlarged head portion with a hexagonal hole formed through the top face to receive an Allen key and a self-tapping threaded end; being long enough such that the head projects outside the shaft of the femur and the self tapping portion cuts a path into the opposing wall of the femur.

9. The device as claimed in claim 1, wherein the wall of the hip screw being cut in such a manner that no significant material is removed by this incision to the wall of the rod; the leading side of the incision is the swaged inwards leading a longitudinally facing window in through which the wire emerges; the guiding means being provided by the shaped leading end of the wire and the inwardly deformed edge of the exit window.

10. The device as claimed in claim 1, wherein the hip screw being provided with an annular member fitted within the hip screw; the said annular member has shaped surface arranged to cooperate with the wires; the said annular member projects inwardly of the hip screw such that the leading edges of the wires engage the annular member before reaching the opening in the wall of the hip screw; a tunnel is created which gives further support to the emerging wire, minimizing movement relative to the hip screw in all directions; a precise plug fitted into the end of the hip screw accomplishes this.

11. The device as claimed in claim 10, wherein the plug is substituted with an annular member comprising a sleeve welded inside the rod.

12. The device as claimed in claim 10, wherein the plug is substituted with separate inserts, fitting the machine slots being separately welded, brazed, soldered or snug fit into place.

13. The device as claimed in claim 1, wherein the tear drop slots are a tear drop shaped hole that is substituted with a straight hole.

14. The device as claimed in claim 1, wherein the elongate device comprising of two flat pre-sprung flats projecting through the hip screw; the separate flat pre-sprung flats not being welded to each other but welded only at the hip screw, which consist of a single hole or slot.

15. The device as claimed in claim 1, wherein the elongate device comprising of a plurality of square cross-section wires with corresponding number of slots or holes.

16. The device as claimed in claim 1, wherein the elongate device comprising of plurality of round cross section wires with corresponding number of slots or holes.

\* \* \* \* \*